United States Patent [19]

Toy et al.

[11] Patent Number: 4,945,063
[45] Date of Patent: Jul. 31, 1990

[54] METHOD FOR DETECTING ORGANIC COMPOUNDS BY PHOTOACOUSTIC CONVERSION

[76] Inventors: Madeline S. Toy, 4190 Manuela Ave., Palo Alto, Calif. 94306; Melvin K. Carter, 129 Worcester Loop, Los Gatos, Calif. 95032

[21] Appl. No.: 247,710

[22] Filed: Sep. 22, 1988

[51] Int. Cl.[5] .................... G01N 33/44; B01J 19/08; B01J 19/10
[52] U.S. Cl. ..................................... 436/85; 436/108; 436/119; 436/124; 436/139; 436/905; 204/157.15
[58] Field of Search .................. 204/157.15, 157.62, 204/157.81, 157.82, 157.94, 1 T; 436/85, 108, 119, 124, 139, 905

[56] References Cited

U.S. PATENT DOCUMENTS 4,144,152  3/1979  Kitchens ..................... 204/157.15

FOREIGN PATENT DOCUMENTS 0257170  3/1988  European Pat. Off. ....... 204/157.15

OTHER PUBLICATIONS

Weissler A., The Journal of the Accoustical Society of America, vol. 25, No. 4, Jul. 1953, pp. 651–657.

Primary Examiner—John F. Niebling
Assistant Examiner—Ben C. Hsing
Attorney, Agent, or Firm—Flehr, Hohbach, Test, Albritton & Herbert

[57] ABSTRACT

A method is provided for detecting the presence of organic materials in an aqueous sample. The materials are decomposed by simultaneous exposure to ultraviolet radiation and acoustic energy to decompose the materials to simple decomposition products. The simple decomposition products such as ammonium ion, halogen ion, alkyl ammonium ions, or sulfate ions, are then detected by conventional analytical devices and methods.

11 Claims, 1 Drawing Sheet

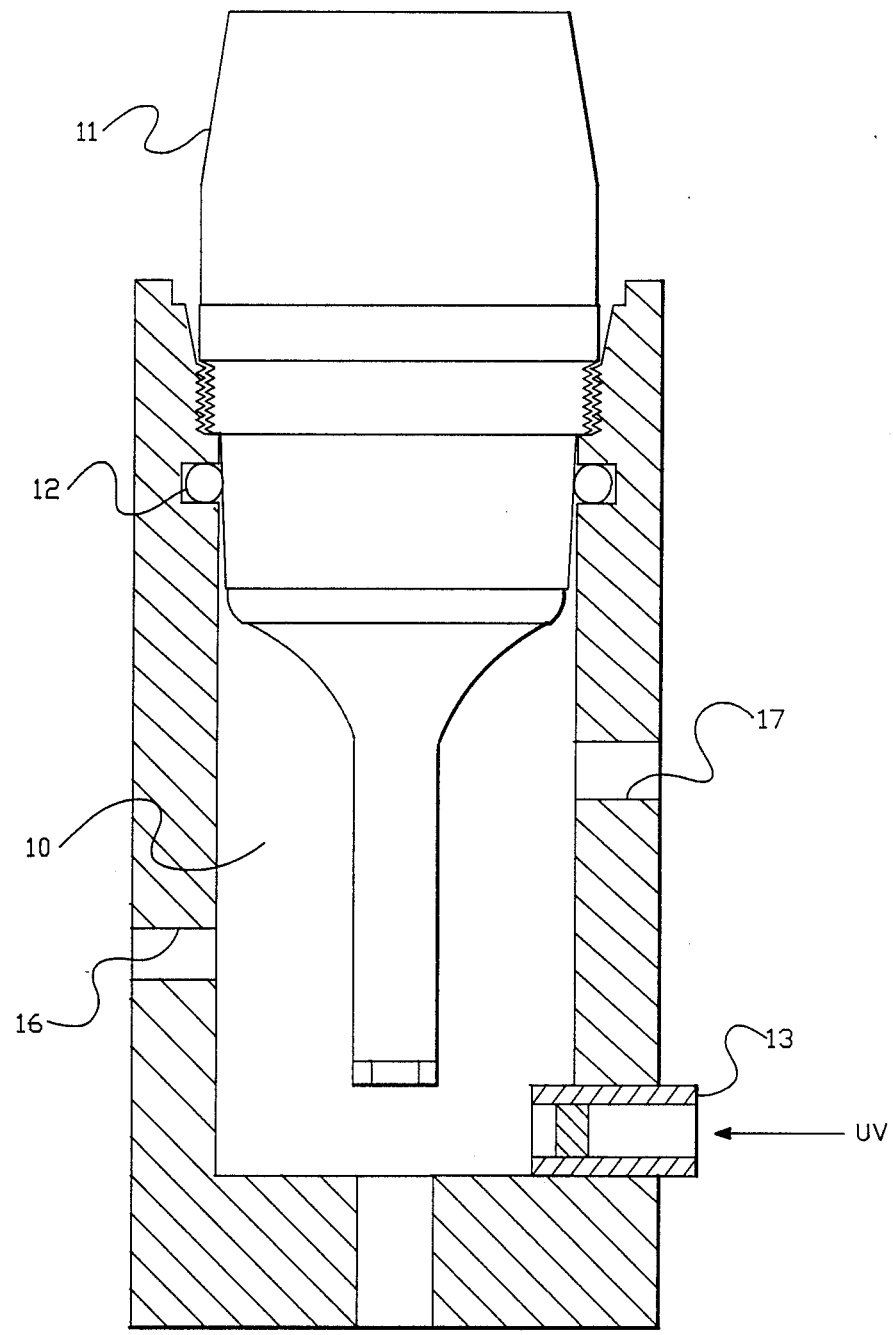

METHOD FOR DETECTING ORGANIC COMPOUNDS BY PHOTOACOUSTIC CONVERSION

The present application is directed to a method for detecting organic materials present in an aqueous medium by photoacoustic decomposition.

BACKGROUND OF THE INVENTION

The detection of impurities in water systems is always generally of interest and, in particular the detection of trace impurities- in nuclear power plant water flow systems has been of recent interest because of the need for more accurate and timely analytical data. For example, the water in a nuclear power plant flow system is usually purified by ion exchange resins. However, the resin columns sometimes leak and it would be therefore desirable to be able to obtain rapid and accurate information regarding the time and amount of the resin leakage since resin leakage places organic impurities (the resin) back into the water system, which, in turn decompose during the steam cycle, thereby releasing ionic species leading to corrosion. Therefore it is extremely important to have an on-line resin leakage detection system for plant condensate/feed water streams before the steam cycle in order to provide a decision-maker at the plant with exact information regarding the time and amount of leakage and with appropriate time to take action to reduce the resin leakage.

It is thus an object of the present invention to provide a method for detecting organic materials present in an aqueous medium which provides rapid and accurate results.

It is a further object of the present invention to provide a method for detecting organic materials present in an aqueous medium by decomposition of the organic materials to simple decomposition products which can be readily detected by conventional analytical detectors.

These and other objects will be present from the following description and appended claims and from practice of the invention.

SUMMARY OF THE INVENTION

The present invention provides a method for detecting organic materials present in an aqueous medium comprising the steps of exposing the aqueous medium containing the organic materials simultaneously to ultraviolet radiation and acoustic energy to decompose the organic materials to simple decomposition products, then detecting the presence of one or more predetermined decomposition products in the aqueous medium by an analytical monitoring method or device.

DESCRIPTION OF THE INVENTION

BRIEF DESCRIPTION OF THE DRAWING

In the FIGURE there is shown a partial cutaway elevation of a sample-holding device for exposure of an aqueous sample to UV and acoustic energy.

Organic materials present (i.e., suspended, dissolved or present in a separate phase) in aqueous media are exposed simultaneously to ultraviolet radiation and acoustic energy to decompose those materials to simple species which are readily detectable by conventional detection methods or devices. The wavelength of the ultraviolet radiation utilized in accordance with the present invention is not critical, as long as it is in the ultraviolet range. Typically, for the purpose of detecting an organic material, the volume of the aqueous sample which is tested is not large, therefore the intensity of the ultraviolet radiation source need not be exceedingly high. For example a 200 watt ultraviolet source such as a mercury xenon lamp will usually be sufficient.

A source of acoustic energy may be a typical sonicator, many of which are commercially available. The range of acoustic energy which may be utilized will generally be from 10 to 50 kHz, preferably 18 to 22 kHz. For convenience, a typical frequency will be about 20 kHz. Typically the aqueous sample will flow by the face of the sonicator horn. A portion of the chamber containing the sample will accommodate a window transparent to ultraviolet radiation. The flow rate of the aqueous sample through the chamber will of course depend upon the size of the chamber and the intensity of the simultaneous ultraviolet radiation and acoustic energy. The outlet from the chamber will then flow to a concentrator, if needed, or directly to one or more analytical instruments for taking on-line measurements of preselected decomposition products which may be present in the sample. The analytical instruments will depend upon the species which is desired to be monitored.

In a particularly preferred embodiment of the invention, trace amount of mixed cation and anion exchange resins present in the aqueous medium may be detected by monitoring a decomposition product of the anion exchange resin by ultraviolet radiation and acoustic energy, such as methylamine, ordinarily present as a methyl ammonium ion. A methyl ammonium ion may be detected by ion chromatograph in a typical instrument such as a Dionex 4000i.

Other parameters may be monitored, such as total organic carbon measured by, for example, a commercial Anatel A-100 Organics Analyzer.

The presence of trace amounts of cation resins in the water sample may be monitored by detecting the presence of, for example, sulfate ions which result from the degradation of typical cation resins by ultraviolet and acoustic energy. If desired, presence of other contaminants in the water may be detected by their degradation products. The presence of halogenated hydrocarbons may be detected by the presence of the decomposition product halide ions; urea may be detected by the presence of the decomposition product ammonium ion, and so forth.

The duration of the simultaneous exposure of the sample to ultraviolet radiation and acoustic energy will usually be less than a few minutes. The duration of exposure may be adjusted by one of ordinary skill in the art by adjusting the flow rate of the sample through the resonant body and by conventional standardization of the instruments using known contaminated samples.

Referring to the accompanying FIGURE there is shown a partial cross-sectional view of a device which may be utilized to simultaneously expose an aqueous sample to acoustic energy and ultraviolet radiation. A chamber 10 has one open end which is tightly fitted with a conventional sonicator 11. The sonicator 11 is tightly fitted, for example by use of an O-ring 12. At the other end of the chamber 10 there is an orifice which is fitted with an insert 13 which holds an ultraviolet transparent window 14, such as quartz. The acoustic energy is focused by the sonicator 11 at sample inlet 15 and the ultraviolet radiation source (not shown) is focused through window 14 transversely to inlet 15. The aqueous sample is thus flowed into the chamber 10 whereupon the sample is simultaneously exposed to acoustic energy and ultraviolet radiation. As the exposed sample level rises within the chamber 10 the sample may be withdrawn through sample withdrawal port 16 and concentrated, if needed, then conducted to the analytical devices (not shown). Port 17 is provided as an overflow release to prevent the filling of the chamber 10.

Having described the preferred embodiments of the present invention the following examples are provided but are not intended to limit the invention in any way.

EXAMPLE 1

A photosonication cell consisting of a self-cleaning concentrator and utilizing a quartz ultraviolet transparent lens for transmission of ultraviolet light into the sample chamber was utilized with the outlets directed to sampling effluent flow into two analytical instruments, the first being a Dionex 4000i for gradient ion chromatography and an Anatel A-100 Organics Analyzer for on-line total organic carbon measurement. The self-cleaning concentrator consisted of two 8-inch diameter stainless steel porous metal plates (0.5 micron pore size). A 200 watt high pressure mercury xenon lamp was the radiation source. The sonicator model W-370 was purchased from Heat Systems - Ultrasonics, Inc. The titanium horn resonant body was vibrated at 20 kHz and served as the primary stage for acoustic energy through the system. A Dowex 50W-X2, 50 to 100 mesh, cation resin and Dowex 1-4X, 20 to 50 mesh anion resin, both from Poly Sciences, Inc., were crushed and mixed at a 1:1 ratio by weight. The water used in the sample was deionized by using two nuclear grade mixed bed resin columns and a charcoal filter. A 10 milligram crushed mixed resin in water sample was subjected first to the combined ultrasound and ultraviolet light in the -photosonicator, and secondly to ultraviolet alone in separate experiments. The ion chromatogram of the samples subjected to photolysis alone showed at least about a fifty times difference in peak heights for the methyl ammonium peak showing that much more methyl ammonium ion is produced by photosonication versus photolysis alone.

EXAMPLE 2

A photosonicator sampler was put on-line at Trojan Nuclear Power Plant (Portland General Electric) in Rainier, Oreg. for sampling from the demineralizer vessel. In this instance the photosonicator chamber held 12 ml of aqueous filtered resin fragments and the exchange rate of the 12 ml volume was about once every three minutes, removing about half the degraded organics and ions with a sampling effluent flow rate of 4 ml/min. The frequency of the ion chromatography analyses was about every ten minutes. Therefore about 90% of the resin material was removed from the photosonicator chamber between each ion chromatography analysis. The effluent sample from the laboratory unit was measured by ion chromatograph for methylamine cations about every ten minutes. The methylamine cations, which were degraded from the anion resin of the mixed powdered resins in the plant condensate/feed water system, were measured by ion chromatograph at a sensitivity level of 0.5 to 5 ppb (0.5 to 5 $\times 10^{-9}$). The measured concentration of methylamine cation by ion chromatography is directly related to the concentration of the anion resin leakage, which is at a certain ratio to the cation resin leakage. At the Trojan plant, for example, the aqueous cation-to-anion ratio of 3:1 to 2:1 is used depending upon the chemistry of the condensate/feed water system. The concentration of the anion resin leakage is determined to be the concentration of the methyl ammonium times a number between 10 to 100 divided by a preconcentration factor of 100 or more. An anion resin in leakage detection concentration was determined with a preconcentration factor of 100 to be 0.05 to 5 ppb. When the photosonication treatment was turned off no methyl ammonium cation was detected by ion chromatograph. Simultaneously the main resin in leakage from the plant's condensate demineralizer outlet was collected through a 2 micron pore Teflon filter for 24 hours at a flow rate of 200 ml/min. The collected resin filter was analyzed by radio tracer technique. The cation resin was found to be 1.4 micrograms per filter and the anion resin was found to be 2.6 micrograms per filter. The estimated average anion resin concentration over 24 hours was calculated to be 6.45 ppt. The methylamine cations were measured by the ion chromatograph at the sensitivity level of 0.2 to 10 ppb with a preconcentration factor of 150 to detect 0.013 to 6.6 ppb anion resin leakage.

What is claimed is:

1. A method for detecting residues of organic resins in an aqueous sample comprising the steps of simultaneously exposing said aqueous sample suspected of containing said resins to ultraviolet radiation and acoustic energy to decompose said organic resins to simple decomposition products, and analyzing said sample to detect at least one of said simple decomposition products, if present.

2. A method according to claim 1 wherein said organic resins comprise anion exchange resins.

3. A method according to claim 2 wherein said simple decomposition products comprise methyl ammonium ion.

4. A method according to claim 1 wherein said organic resins comprise cation exchange resins.

5. A method according to claim 4 wherein said simple decomposition products comprise sulfate ions.

6. A method according to claim 1 wherein said organic resins comprise halogenated hydrocarbons.

7. A method according to claim 6 wherein said simple decomposition products comprise halogen ions.

8. A method according to claim 1 wherein said organic resins comprise urea.

9. A method according to claim 8 wherein said simple decomposition products comprise ammonium ions.

10. A method according to claim 1 wherein said acoustic energy is in the range of about 10 to 50 kHz.

11. A method according to claim 10 where said acoustic energy is in the range of 18 to 22 kHz.

* * * * *